(12) United States Patent
Krupinski et al.

(10) Patent No.: US 11,274,086 B2
(45) Date of Patent: Mar. 15, 2022

(54) AMPLIFICATION OF NUCLEIC ACIDS

(71) Applicant: Abbott Molecular Inc., Des Plaines, IL (US)

(72) Inventors: Tomasz Krupinski, Des Plaines, IL (US); Jeffrey D. Wuitschick, Des Plaines, IL (US); Shihai Huang, Des Plaines, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 58 days.

(21) Appl. No.: 16/722,239

(22) Filed: Dec. 20, 2019

(65) Prior Publication Data
US 2020/0207729 A1 Jul. 2, 2020

Related U.S. Application Data

(60) Provisional application No. 62/786,860, filed on Dec. 31, 2018.

(51) Int. Cl.
| | |
|---|---|
| *C07D 275/03* | (2006.01) |
| *C12N 9/12* | (2006.01) |
| *C12Q 1/6806* | (2018.01) |
| *C12Q 1/682* | (2018.01) |
| *C12Q 1/6848* | (2018.01) |
| *C12Q 1/6851* | (2018.01) |
| *C12Q 1/686* | (2018.01) |

(52) U.S. Cl.
CPC ......... *C07D 275/03* (2013.01); *C12N 9/1247* (2013.01); *C12Q 1/682* (2013.01); *C12Q 1/686* (2013.01); *C12Q 1/6806* (2013.01); *C12Q 1/6848* (2013.01); *C12Q 1/6851* (2013.01); *C12Q 2523/10* (2013.01); *C12Q 2531/113* (2013.01)

(58) Field of Classification Search
CPC .... C12Q 1/6806; C12Q 1/682; C12Q 1/6848; C12Q 1/6851; C12Q 1/686; C12Q 2523/10; C12Q 2531/113; C12Q 2527/125; C12N 9/1247; C07D 275/03
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 6,329,178 B1 | 12/2001 | Patel et al. |
| 6,395,524 B2 | 5/2002 | Loeb et al. |
| 6,602,695 B2 | 8/2003 | Patel et al. |
| 8,703,445 B2 | 4/2014 | Collier et al. |
| 2007/0048748 A1 | 3/2007 | Williams et al. |
| 2013/0252232 A1* | 9/2013 | Leckie .............. C12Q 1/706 435/5 |
| 2013/0323727 A1 | 12/2013 | Huang et al. |
| 2017/0044594 A1 | 2/2017 | Wang et al. |

FOREIGN PATENT DOCUMENTS

| | | |
|---|---|---|
| WO | WO-2016183012 | 11/2016 |
| WO | WO-2017011565 | 1/2017 |

OTHER PUBLICATIONS

Abu-Al Soud, et al., "Capacity of nine thermostable DNA polymerases to mediate DNA amplification in the presence of PCR-Inhibiting samples" Appl Environ Microbiol. (1998) 64: 3748-53.
Myers, et al., "Reverse transcription and DNA amplification by a Thermus thermophilus DNA polymerase" Biochemistry (1991) 30: 7661-66.
Bustin, "Absolute quantification of mRNA using real-time reverse transcription polymerase chain reaction assays" Journal of Molecular Endocrinology (2000) 25: 169-93.
2-methyl-4-isothiazolin-3-one, CAS No. 2682-20-4.
Sigma Aldrich, "ProClin™ 950 Preservative for Diagnostic Reagents" (2015) 2 pages.
Sigma Aldrich, SAFC Supply Solutions™, ProClin™ 950 Preservative for Diagnostic Reagents, Directions for Use (2005) 1 page.
Abbott Molecular Inc., "Abbott Real Time HIV-1", 2011, 1-11.
International Search Report and Written Opinion issued in corresponding application PCT/US2019/067749, dated Apr. 28, 2020, 11 pages.

* cited by examiner

*Primary Examiner* — David C Thomas
(74) *Attorney, Agent, or Firm* — Casimir Jones, S.C.; Kirk J. Hogan

(57) ABSTRACT

Provided herein is technology relating to amplification of nucleic acids and particularly, but not exclusively, to compositions and methods for doing improving the polymerase chain reaction and providing reagents for polymerase chain reaction with improved stability.

12 Claims, 3 Drawing Sheets

AMPLIFICATION OF NUCLEIC ACIDS

This application claims priority to U.S. provisional patent application Ser. No. 62/786,860, filed Dec. 31, 2018, which is incorporated herein by reference in its entirety.

FIELD

Provided herein is technology relating to amplification of nucleic acids and particularly, but not exclusively, to compositions and methods for conducting polymerase chain reactions and providing reagents for polymerase chain reactions with improved stability.

BACKGROUND

Many in vitro diagnostic assays based on the polymerase chain reaction (PCR) rely on fast polymerase enzymes. Accordingly, fast PCR enzymes have been engineered to deliver increased speed and processivity, but may also exhibit an increased propensity to generate spurious amplification products from non-specific priming and/or dimer-primer formation. The formation of these non-specific products can negatively impact the overall efficiency of PCR and/or RT-PCR by interfering with target amplification and/or by depleting reaction resources.

Numerous technologies have been developed to improve the amplification of nucleic acids, e.g., by PCR. For example, compositions and methods are available that reduce non-specific priming and/or dimer-primer formation in the PCR. One particular strategy comprises use of "hot start" primers and "hot start" dNTPs that are produced with a thermolabile chemical modification that prevents extension prior to incubation at an elevated temperature at the beginning of a thermal cycling program. However, "hot start" mechanisms can negatively impact RT-PCR because most reverse transcriptase enzymes are irreversibly inactivated by the elevated temperature of the "hot start" thermal cycling step. Other PCR and RT-PCR enhancers include betaine, tetramethylammonium chloride (TMAC), formamide, and dimethyl sulfoxide (DMSO), which generally function by increasing the specificity of hybridization and increasing the $T_m$ of primers/probes.

Although non-specific priming and/or dimer-primer formation can occur during reverse transcription and/or PCR steps, it can also occur during master mix preparation and during reaction setup. These problems are challenges to manufacturers of PCR and RT-PCR assays, especially when manufacturing steps require assembly of complete master mixes, e.g., comprising enzymes, activation reagent, primers, and/or probes) as a single bulk reagent. The long lead times typically associated with preparing, mixing, and filling such bulk reagents can increase the likelihood non-specific priming and/or dimer-primer formation during manufacturing and, thereby, lead to a decline in assay performance.

SUMMARY

The technology provided herein relates to use of 2-methyl-4-isothiazolin-3-one (MIT) as an enhancer of PCR. MIT has been used as a biocide (e.g., in the preservative sold under the trade name of PROCLIN 950). The technology provided herein comprises use of MIT as an enhancer of the PCR and to provide increased stability of activated PCR and/or RT-PCR master mixes (e.g., during master mix reagent manufacturing). During the development of embodiments of the technology provided herein, experiments were conducted to test the use of MIT in PCR to disrupt and/or preventing non-specific priming and/or primer-dimer formation. Data collected during these experiments demonstrated that inclusion of MIT in PCR/RT-PCR reactions prevents and/or disrupts non-specific priming and/or primer-dimer formation, thereby reducing the accumulation of non-specific product (see, e.g., Example 1 and Example 2). Further, these data indicated that MIT provides a general enhancement of PCR/RT-PCR assay performance (see, e.g., Example 3 and Example 4) and improved stability of activated master mix (see, e.g., Example 5).

Accordingly, the technology finds use as a general enhancer in PCR and/or RT-PCR applications; and 2) to improve stability of PCR and/or RT-PCR master mixes (e.g. during master mix reagent manufacturing). In some embodiments, the technology provides a nucleic acid amplification composition. In some embodiments, the nucleic acid amplification composition comprising a polymerase, one or more primers (e.g., a first primer and a second primer), nucleotides, and 0.0001 to 0.1% (w/w) 2-methyl-4-isothiazolin-3-one (MIT) (e.g., 0.001 to 0.01% (w/w) MIT)). In some embodiments, the nucleic acid amplification composition comprises 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT. In some embodiments, the nucleic acid amplification composition further comprises a target template.

In some embodiments, the nucleic acid amplification composition further comprises a detectably labeled probe or intercalating dye. The technology is not limited in the detectable label or intercalating dye. For instance, in some embodiments, the detectable label is a fluorescent moiety, e.g., a dye that can be synthesized or obtained commercially (e.g., from Operon Biotechnologies, Huntsville, Ala.). A large number of dyes (greater than 50) are available for application in fluorescence excitation applications. These dyes include those from the fluorescein, rhodamine, AlexaFluor, Bodipy, Coumarin, and Cyanine dye families. Specific examples of fluorophores include, but are not limited to, FAM, TET, HEX, Cy3, TMR, ROX, VIC (e.g., from Life Technologies), Texas red, LC red 640, Cy5, and LC red 705. In some embodiments, dyes with emission maxima from 410 nm (e.g., Cascade Blue) to 775 nm (e.g., Alexa Fluor 750) are available and can be used. Of course, one of ordinary skill in the art will recognize that dyes having emission maxima outside these ranges may be used as well. In some cases, dyes ranging between 500 nm to 700 nm have the advantage of being in the visible spectrum and can be detected using existing photomultiplier tubes. In some embodiments, the broad range of available dyes allows selection of dye sets that have emission wavelengths that are spread across the detection range. Detection systems capable of distinguishing many dyes are known in the art.

In some embodiments, the nucleic acid amplification composition does not comprise a primer dimer (e.g., comprising said first primer and said second primer) (e.g., a detectable level of primer dimer).

In some embodiments, the technology provides an oligonucleotide reagent. In some embodiments, the oligonucleotide reagent comprises one or more primers (e.g., a first primer and a second primer), a detectably labeled probe, nucleotides, and 0.0001 to 0.1% (w/w) MIT. In some embodiments, the oligonucleotide reagent comprises a first primer, a second primer, a detectably labeled probe, nucleotides, and 0.001 to 0.01% (w/w) MIT. In some embodiments, the oligonucleotide reagent comprises a first primer, a second primer, a detectably labeled probe, nucleotides, and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT. In some embodiments, the oligonucleotide reagent further comprises a second detectably labeled probe (e.g., comprising a fluorescent moiety as described above). In some embodiments, the oligonucleotide reagent further comprises a reference dye (e.g., a fluorescent dye as described above). In some embodiments, the oligonucleotide reagent further comprises a third primer and/or a fourth primer.

In some embodiments, the technology provides kits (e.g., kits for detecting a nucleic acid by realtime PCR (e.g., RT-PCR)). For example, in some embodiments, kits are provided herein that comprise an oligonucleotide reagent comprising a one or more primers (e.g., first primer and a second primer), a detectably labeled probe, nucleotides, and 0.0001 to 0.1% (w/w) MIT; and an activation reagent comprising manganese chloride and 0.0001 to 0.1% (w/w) MIT. In some embodiments, kits further comprise a thermostable polymerase in a buffered solution. In some embodiments, the thermostable polymerase is rTth polymerase. However, the technology is not limited to this particular polymerase and comprises embodiments comprising other polymerases known in the art (e.g., as described herein). In some embodiments, kits further comprise an internal control comprising a control nucleic acid and 0.0001 to 0.1% (w/w) MIT.

The technology relates to providing shelf-stable reagents (e.g., reagents for realtime PCR). In some embodiments, the technology provides a commercial scale mastermix composition having a volume greater than 10 mL (e.g., greater than 100 mL, greater than 1 liter) and comprising a first primer, a second primer, a detectably labeled probe, nucleotides, and 0.0001 to 0.1% (w/w) MIT (e.g., 0.001 to 0.01% (w/w) MIT). In some embodiments, the commercial scale mastermix composition comprises a first primer, a second primer, a detectably labeled probe, nucleotides, and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT.

In some embodiments, the technology provides a commercial scale mastermix composition having a volume greater than 10 mL (e.g., greater than 100 mL, greater than 1 liter) and comprising manganese chloride and 0.0001 to 0.1% (w/w) MIT. (e.g., 0.001 to 0.01% (w/w) MIT). In some embodiments, the commercial scale mastermix composition comprises manganese chloride and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT.

In some embodiments, the technology provides methods for detecting a nucleic acid (e.g., by realtime PCR). For example, in some embodiments, methods comprise providing a reaction composition comprising a polymerase, a first primer, a second primer, nucleotides, and 0.0001 to 0.1% (w/w) MIT (e.g., 0.001 to 0.01% (w/w) MIT). In some embodiments, the methods comprise providing a reaction composition comprising a polymerase, a first primer, a second primer, nucleotides, and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT. In some embodiments, methods further comprise adding a sample to said reaction composition. In some embodiments, methods further comprise providing a detectably labeled probe (e.g., wherein said label is a fluorescent moiety as described herein) or an intercalating dye. In some embodiments, methods further comprise thermocycling said reaction composition. In some embodiments, methods further comprise measuring the fluorescence emission of said reaction composition.

In some embodiments, methods for detecting a nucleic acid (e.g., by realtime PCR) comprise storing a realtime PCR reagent comprising 0.0001 to 0.1% (w/w) MIT (e.g., 0.001 to 0.01% (w/w) MIT) and at least one of a polymerase, a first primer, a second primer, and/or nucleotides for at least 1 day, 1 week, or 1 month. In some embodiments, the realtime PCR reagent is used to prepare a reaction composition comprising a polymerase, a first primer, a second primer, nucleotides, and 0.0001 to 0.1% (w/w) MIT (e.g., 0.001 to 0.01% (w/w) MIT). In some embodiments, the methods comprise using a realtime PCR reagent to prepare a reaction composition a polymerase, a first primer, a second primer, nucleotides, and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT.

In some embodiments, the technology provides a method of producing a realtime PCR reagent comprising mixing 0.0001 to 0.1% (w/w) MIT (e.g., 0.001 to 0.01% (w/w) MIT) with at least one of a polymerase, a first primer, a second primer, and/or nucleotides. In some embodiments, the method of producing a realtime PCR reagent comprises mixing 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT with with at least one of a polymerase, a first primer, a second primer, and/or nucleotides. In some embodiments, the realtime PCR reagent has a volume greater than 10 mL (e.g., greater than 100 mL, greater than 1 liter). In some embodiments, the method of producing a realtime PCR reagent comprises storing said realtime PCR reagent for at least 1 day, 1 week, or 1 month. In some embodiments, the method of producing a realtime PCR reagent comprises mixing into the realtime PCR reagent a reference dye, a detectably labeled probe, an intercalating dye, a third primer, and/or a fourth primer.

In some embodiments, the technology provides systems for detecting a nucleic acid. In some embodiments, the system comprises an oligonucleotide reagent comprising a first primer, a second primer, a detectably labeled probe, nucleotides, and 0.0001 to 0.1% (w/w) MIT; and an activation reagent comprising manganese chloride and 0.0001 to 0.1% (w/w) MIT. In some embodiments, the system further comprises a realtime thermocycler. Some embodiments of the technology provided herein further comprise functionalities for collecting, storing, and/or analyzing data. For example, in some embodiments the device comprises a processor, a memory, and/or a database for, e.g., storing and executing instructions, analyzing data, performing calculations using the data, transforming the data, and storing the data. Moreover, in some embodiments a processor is configured to control the device. In some embodiments, the processor is used to initiate and/or terminate the measurement and data collection. In some embodiments, the device comprises a user interface (e.g., a keyboard, buttons, dials, switches, and the like) for receiving user input that is used by the processor to direct a measurement. In some embodiments, the device further comprises a data output for transmitting data to an external destination, e.g., a computer, a display, a network, and/or an external storage medium. Some embodiments provide that the device is a small, handheld, portable device incorporating these features and components. In some embodiments, the system further comprises a computer configured to determine a Ct value. In some embodiments, the systems further comprise a thermostable polymerase in a buffered solution. In some embodiments, the thermostable polymerase is rTth polymerase.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings. In the figures, "Proclin" refers to PROCLIN 950 (9.5% (w/w) MIT dissolved in water).

Figure 1:
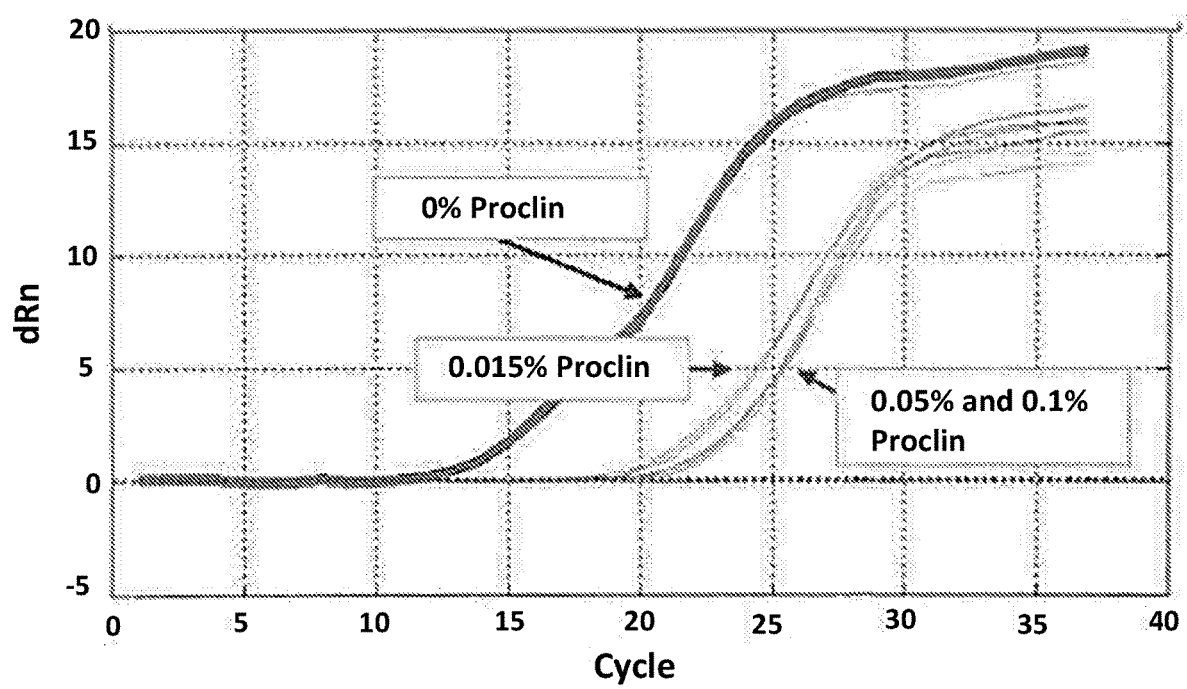
FIG. 1 is a plot of RT-PCR data indicating that including MIT in master mixes reduces the accumulation of non-specific product. The plot shows dRn as a function of cycle number for samples comprising 0, 0.015, 0.05, and 0.1% (w/w) PROCLIN 950 (corresponding to 0, 0.0015, 0.005, and 0.01% (w/w) MIT concentrations, respectively).

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to amplification of nucleic acids and particularly, but not exclusively, to compositions and methods for conducting the polymerase chain reaction and providing reagents for polymerase chain reactions with improved stability.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "about", "approximately", "substantially", and "significantly" are understood by persons of ordinary skill in the art and will vary to some extent on the context in which they are used. If there are uses of these terms that are not clear to persons of ordinary skill in the art given the context in which they are used, "about" and "approximately" mean plus or minus less than or equal to 10% (w/w) of the particular term and "substantially" and "significantly" mean plus or minus greater than 10% (w/w) of the particular term.

As used herein, disclosure of ranges includes disclosure of all values and further divided ranges within the entire range, including endpoints and sub-ranges given for the ranges.

As used herein, the suffix "-free" refers to an embodiment of the technology that omits the feature of the base root of the word to which "-free" is appended. That is, the term "X-free" as used herein means "without X", where X is a feature of the technology omitted in the "X-free" technology. For example, a "calcium-free" composition does not comprise calcium, a "mixing-free" method does not comprise a mixing step, etc.

Although the terms "first", "second", "third", etc. may be used herein to describe various steps, elements, compositions, components, regions, layers, and/or sections, these steps, elements, compositions, components, regions, layers, and/or sections should not be limited by these terms, unless otherwise indicated. These terms are used to distinguish one step, element, composition, component, region, layer, and/or section from another step, element, composition, component, region, layer, and/or section. Terms such as "first", "second", and other numerical terms when used herein do not imply a sequence or order unless clearly indicated by the context. Thus, a first step, element, composition, component, region, layer, or section discussed herein could be termed a second step, element, composition, component, region, layer, or section without departing from technology.

As used herein, "dRn" refers to the magnitude of the fluorescence signal generated during a RT-PCR at each time point and/or cycle number. The dRn value is determined by the following formula (Rn+)−(Rn−). Rn (normalized reporter signal) is the fluorescence emission intensity of the reporter dye divided by the fluorescence emission intensity of the passive reference dye. Rn+ is the Rn value of a reaction containing all components, including the template. Rn− is the Rn value of an unreacted sample. The Rn− value can be obtained from the early cycles of a RT-PCR (e.g., the cycles prior to a significant increase in fluorescence) or in a reaction that does not comprise template.

As used herein, the term "Ct" or "threshold cycle" refers to the cycle number at which the fluorescence generated within a reaction crosses a threshold. The Ct is inversely correlated to the logarithm of the initial copy number. The Ct value assigned to a particular reaction thus reflects the point during the reaction at which a sufficient number of amplicons have accumulated.

As used herein, the term "intercalating dye" or "dsDNA-binding agent" refers to a molecule that has a higher fluorescence emission when bound to double-stranded DNA (dsDNA) relative to when not bound to dsDNA. Thus, in some real-time PCR, the fluorescence intensity increases proportionally to dsDNA (amplicon) concentration. An exemplary dsDNA-binding agent is SYBR Green I, which is a fluorogenic minor groove binding dye that emits little fluorescence when in solution but emits a strong fluorescent signal upon binding to double-stranded DNA. Similar dsDNA-binding fluorescent dyes include EvaGreen and LCGreen.

As used herein, the term "fast PCR" refers to a modified PCR protocol that is complete in a run time of less than 90 minutes (e.g., 30, 35, 40, 45, 50, 55, or 60 minutes or less) due to improvements in amplicon design, reagent chemistry, thermocycling conditions, and instrumentation (e.g., PCR machines with fast ramping rates).

As used herein, the term "no amplification controls" or "NAC" is a control that does not comprise a polymerase enzyme. In mRNA analysis, NAC is a mock reverse transcription containing all the RT-PCR reagents except the reverse transcriptase. If cDNA or genomic DNA is used as a template, a reaction mixture lacking Taq polymerase can be included in the assay as NAC. No product should be synthesized in the NAC.

As used herein, the term "no template controls" or "NTC" is a control that does not comprise a sample or target nucleic acid. A NTC includes all the RT-PCR reagents except the RNA template. No product should be synthesized in the NTC.

As used herein, the term "nucleic acid target" or "target template" or "target nucleic acid" refers to the DNA or RNA sequence that is or is intended to be amplified. The nucleic acid sample used to amplify the target sequence is called template. In a typical qPCR, the cDNA sample included in the reaction is the template.

As used herein, the term "realtime PCR" refers to the continuous collection of fluorescent signal from polymerase chain reaction throughout cycles.

As used herein, the term "threshold" refers to the fluorescent signal level that is considered to be above background level or noise. In some embodiments, the threshold is 10× the standard deviation of Rn for the early PCR cycles and/or is set in the region associated with an exponential growth of PCR product and not as high as the linear or plateau sections of the curve. In some embodiments, the threshold is above the highest baseline signal level.

As used herein, a "nucleic acid" shall mean any nucleic acid molecule, including, without limitation, DNA, RNA, and hybrids thereof. The nucleic acid bases that form nucleic acid molecules can be the bases A, C, G, T and U, as well as derivatives thereof. Derivatives of these bases are well known in the art. The term should be understood to include, as equivalents, analogs of either DNA or RNA made from nucleotide analogs. The term as used herein also encompasses cDNA, that is complementary, or copy, DNA produced from an RNA template, for example, by the action of a reverse transcriptase.

Reference to a base, a nucleotide, or to another molecule may be in the singular or plural. That is, "a base" may refer to a single molecule of that base or to a plurality of the base, e.g., in a solution.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually, oligonucleotides range in size from a few monomeric units, e.g. 3-4, to several hundreds of monomeric units. Whenever a polynucleotide such as an oligonucleotide is represented by a sequence of letters, such as "ATGCCTG", it will be understood that the nucleotides are in 5' to 3' order from left to right and that "A" or "a" denotes deoxyadenosine, "C" or "c" denotes deoxycytidine, "G" or "g" denotes deoxyguanosine, and "T" or "t" denotes thymidine, unless otherwise noted. The letters A, C, G, and T may be used to refer to the bases themselves, to nucleosides, or to nucleotides comprising the bases, as is standard in the art.

In some embodiments, nucleic acids comprise a universal or modified base such as deoxyinosine, inosine, 7-deaza-2'-deoxyinosine, 2-aza-2'-deoxyinosine, 2'-O-Me inosine, 2'-F inosine, deoxy 3-nitropyrrole, 3-nitropyrrole, 2'-O-Me 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-O-Me 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'-O-methoxyethyl nebularine, 2'-O-methoxyethyl 5-nitroindole, 2'-O-methoxyethyl 4-nitrobenzimidazole, 2'-O-methoxyethyl 3-nitropyrrole, and combinations thereof.

As used herein, "complementary" generally refers to specific nucleotide duplexing to form canonical Watson-Crick base pairs, as is understood by those skilled in the art. However, complementary also includes base-pairing of nucleotide analogs that are capable of universal base-pairing with A, T, G or C nucleotides and locked nucleic acids that enhance the thermal stability of duplexes. One skilled in the art will recognize that hybridization stringency is a determinant in the degree of match or mismatch in the duplex formed by hybridization.

As used herein, the term "polymerase" refers to an enzyme generally for joining 3'-OH 5'-triphosphate nucleotides, oligomers, and their analogs. Polymerases include, but are not limited to, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase 1, Klenow fragment, *Thermophilus aquaticus* (Taq) DNA polymerase, *Thermus thermophilus* (Tth) DNA polymerase (e.g., recombinant Tth (rTth) polymerase; see, e.g., Abu al-Soud and Radstrom (1998) "Capacity of nine thermostable DNA polymerases to mediate DNA amplification in the presence of PCR-Inhibiting samples" Appl Environ Microbiol. 64: 3748-53; Myers and Gelfand (1991) "Reverse transcription and DNA amplification by a *thermus-thermophilus* DNA-polymerase" Biochemistry 30: 7661-66, each of which is incorporated herein by reference), Vent DNA polymerase (New England Biolabs), Deep Vent DNA polymerase (New England Biolabs), *Bacillus stearothermophilus* (Bst) DNA polymerase, DNA Polymerase Large Fragment, Stoeffel Fragment, 9° N DNA Polymerase, 9° Nm polymerase, *Pyrococcus furiosis* (Pfu) DNA Polymerase, *Thermus filiformis* (Tfl) DNA Polymerase, RepliPHI Phi29 Polymerase, *Thermococcus litoralis* (Tli) DNA polymerase, eukaryotic DNA polymerase beta, telomerase, Therminator polymerase (New England Biolabs), KOD HiFi. DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting and/or molecular evolution, and polymerases cited in U.S. Pat. Appl. Pub. No. 2007/0048748 and in U.S. Pat. Nos. 6,329,178; 6,602,695; and 6,395,524. These polymerases include wild-type, mutant isoforms, and genetically engineered variants such as exo-polymerases; polymerases with minimized, undetectable, and/or decreased 3'→5' proofreading exonuclease activity, and other mutants, e.g., that tolerate labeled nucleotides and incorporate them into a strand of nucleic acid. In some embodiments, the polymerase is designed for use, e.g., in real-time PCR, high fidelity PCR, next-generation DNA sequencing, fast PCR, hot start PCR, crude sample PCR, robust PCR, and/or molecular diagnostics. Such enzymes are available from many commercial suppliers, e.g., Kapa Enzymes, Finnzymes, Promega, Invitrogen, Life Technologies, Thermo Scientific, Qiagen, Roche, etc. In some embodiments, the polymerase has 5'→3' exonuclease activity and can thus degrade a nucleic acid from a 5' end in addition to catalyzing synthesis of a nucleic acid from a 3'-OH of a nucleic acid (e.g., from a primer, e.g., a hairpin primer). In some embodiments the polymerase (e.g., a high-fidelity polymerase) comprises a proof-reading activity, a 3' exonuclease activity, and/or a strand displacement activity, but lacks a 5' exonuclease activity.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method. As used herein, the single stranded (e.g., amplicon-specific) portion of a hairpin primer may serve to prime the synthesis of a nucleic acid.

As used herein, the term "annealing" or "priming" refers to the apposition of an oligodeoxynucleotide or nucleic acid to a template nucleic acid, whereby the apposition enables the polymerase to polymerize nucleotides into a nucleic acid molecule that is complementary to the template nucleic acid or a portion thereof. The term "hybridizing" as used herein refers to the formation of a double-stranded nucleic acid from complementary single stranded nucleic acids. There is no intended distinction between the terms "annealing" and "hybridizing", and these terms will be used interchangeably. The sequences of primers may comprise some mismatches, so long as they can be hybridized with templates and serve as primers. The term "substantially complementary" is used herein to signify that the primer is sufficiently complementary to hybridize selectively to a template nucleic acid sequence under the designated annealing conditions or stringent conditions, such that the annealed primer can be extended by a polymerase to form a complementary copy of the template.

As used herein, the term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention. In particular embodiments, a sample comprises a target nucleic acid.

DESCRIPTION

The compound 2-methyl-4-isothiazolin-3-one (MIT) is a biocidal compound known to suppress microbial respiration through inhibition of specific Krebs cycle enzymes. MIT has a CAS Number 2682-20-4, Empirical Formula of $C_4H_5NOS$, and molecular weight 115.15. MIT has a structure according to

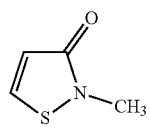

MIT is the active ingredient in the antimicrobial agent PROCLIN 950 (9.5% (w/w) MIT dissolved in water), which is used to prevent microbial growth. Embodiments of the technology provided herein relate to use of MIT to improve PCR. In some embodiments, the technology comprises use of MIT at a concentration that does not have biocidal activity, or has poor or undesirable levels of biocidal activity, in a reagent used for amplification of a nucleic acid (e.g., PCR).

In some embodiments, the technology provides a composition comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid) and MIT. In some embodiments, the technology provides a composition comprising a polymerase and MIT. In some embodiments, the technology provides a composition comprising a probe and MIT. In some embodiments, the technology provides a composition comprising at intercalating dye and MIT. In some embodiments, the technology provides a composition comprising nucleotides (e.g., one or more of dATP, dCTP, dGTP, and dTTP monomers) and MIT. In some embodiments, the technology provides a composition comprising a polymerase, nucleotides (e.g., one or more of dATP, dCTP, dGTP, and dTTP monomers), and MIT. In some embodiments, the technology provides a composition comprising a polymerase, nucleotides (e.g., one or more of dATP, dCTP, dGTP, and dTTP monomers), a probe, and MIT. In some embodiments, the technology provides a composition comprising a polymerase, nucleotides (e.g., one or more of dATP, dCTP, dGTP, and dTTP monomers), an intercalating dye, and MIT.

During the development of embodiments of the technology provided herein, experiments were conducted to test concentrations of MIT in RT-PCR. Data collected during the experiments indicated that nucleic acid amplification (e.g., PCR (e.g., RT-PCR)) was improved by adding MIT to the reaction mixture. In particular, reaction mixtures were produced comprising 0.0015, 0.005, and 0.01% (w/w) MIT. Accordingly, in some embodiments, the technology provides a composition comprising approximately 0.001 to 0.002% (w/w) MIT. In some embodiments, the technology provides a composition comprising approximately 0.0001 to 0.01% (w/w) MIT. In some embodiments, the technology provides a composition comprising approximately 0.0045 to 0.0055% (w/w) MIT. In some embodiments, the technology provides a composition comprising approximately 0.001 to 0.1% (w/w) MIT. In some embodiments, the technology provides a composition for nucleic acid amplification comprising 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT.

In some embodiments, MIT is provided as a mixture in water (e.g., as a solution comprising 9.5% (w/w) MIT dissolved in water and, optionally, other components (e.g., PROCLIN 950)). In some embodiments, the technology provides a composition for nucleic acid amplification comprising 0.010, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, or 0.050 PROCLIN 950.

In some embodiments, the technology provides a composition having a volume ranging from nanoliters to microliters (e.g., a PCR or RT-PCR reaction) to milliliters to centiliters (e.g., a PCR or RT-PCR master mix) to deciliters to liters to decaliters or more (e.g., PCR or RT-PCR reagents produced at a commercial scale). Accordingly, in some embodiments, the technology provides a composition having a volume of 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nl and comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid) and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT.

In some embodiments, the technology provides a composition having a volume of 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µl and comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid) and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT.

In some embodiments, the technology provides a composition having a volume of 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 ml and comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid) and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT.

In some embodiments, the technology provides a composition having a volume of 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 L and comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid) and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT.

In some embodiments, adding MIT to a PCR reaction mixture increases the signal of a realtime PCR (e.g., realtime RT-PCR) by 1.1× to 10× or more (e.g., 1.1×, 1.2×, 1.3×, 1.4×, 1.5×, 1.6×, 1.7×, 1.8×, 1.9×, 2.0×, 2.1×, 2.2×, 2.3×, 2.4×, 2.5×, 2.6×, 2.7×, 2.8×, 2.9×, 3.0×, 3.1×, 3.2×, 3.3×, 3.4×, 3.5×, 3.6×, 3.7×, 3.8×, 3.9×, 4.0×, 4.1×, 4.2×, 4.3×, 4.4×, 4.5×, 4.6×, 4.7×, 4.8×, 4.9×, 5.0×, 5.1×, 5.2×, 5.3×, 5.4×, 5.5×, 5.6×, 5.7×, 5.8×, 5.9×, 6.0×, 6.1×, 6.2×, 6.3×, 6.4×, 6.5×, 6.6×, 6.7×, 6.8×, 6.9×, 7.0×, 7.1×, 7.2×, 7.3×, 7.4×, 7.5×, 7.6×, 7.7×, 7.8×, 7.9×, 8.0×, 8.1×, 8.2×, 8.3×, 8.4×, 8.5×, 8.6×, 8.7×, 8.8×, 8.9×, 9.0×, 9.1×, 9.2×, 9.3×, 9.4×, 9.5×, 9.6×, 9.7×, 9.8×, 9.9×, or 10.0× or more) relative to a PCR reaction that does not comprise MIT.

In some embodiments, adding MIT to a PCR reaction mixture decreases the Ct indicating the presence of a target nucleic acid the signal of a realtime PCR (e.g., realtime RT-PCR) by 1-20 cycles (e.g., 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or 20.0 cycles) relative to a PCR reaction that does not comprise MIT.

In some embodiments, adding MIT to a PCR reaction mixture decreases the amount of non-specific product by 1 to 100% (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60.0, 60.5, 61.0, 61.5, 62.0, 62.5, 63.0, 63.5, 64.0, 64.5, 65.0, 65.5, 66.0, 66.5, 67.0, 67.5, 68.0, 68.5, 69.0, 69.5, 70.0, 70.5, 71.0, 71.5, 72.0, 72.5, 73.0, 73.5, 74.0, 74.5, 75.0, 75.5, 76.0, 76.5, 77.0, 77.5, 78.0, 78.5, 79.0, 79.5, 80.0, 80.5, 81.0, 81.5, 82.0, 82.5, 83.0, 83.5, 84.0, 84.5, 85.0, 85.5, 86.0, 86.5, 87.0, 87.5, 88.0, 88.5, 89.0, 89.5, 90.0, 90.5, 91.0, 91.5, 92.0, 92.5, 93.0, 93.5, 94.0, 94.5, 95.0, 95.5, 96.0, 96.5, 97.0, 97.5, 98.0, 98.5, 99.0, 99.5, 100.0%).

In some embodiments, adding MIT to a PCR reaction mixture delays the formation of non-specific products that fluoresce above a threshold by 1-20 cycles (e.g., 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or 20.0 cycles) relative to a PCR reaction that does not comprise MIT.

In some embodiments, the technology provides methods for producing a composition for amplifying nucleic acids (e.g., by PCR (e.g., by RT-PCR)). For example, in some embodiments, methods comprise providing, producing, and/or obtaining a composition comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid) and MIT. In some embodiments, MIT is provided by providing, producing, and/or obtaining a composition comprising PROCLIN 950.

In some embodiments, methods comprise mixing a composition comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid) and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT.

In some embodiments, methods comprise adding a sample (e.g., a nucleic acid) to a composition comprising MIT. In some embodiments, methods comprise adding a primer to a composition comprising MIT. In some embodiments, methods comprise adding a probe to a composition comprising MIT. In some embodiments, methods comprise adding an intercalating dye to a composition comprising MIT. In some embodiments, methods comprise adding a polymerase to a composition comprising MIT. In some embodiments, methods comprise adding one or more components of a PCR (e.g., polymerase, primers, probes, nucleotides (e.g., one or more of dATP, dCTP, dGTP, and dTTP monomers), intercalating dye, water, buffer, sample, and/or target nucleic acid) to a composition comprising 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT.

In some embodiments, methods comprise adding a composition comprising MIT to a composition comprising a sample (e.g., a nucleic acid). In some embodiments, methods comprise adding a composition comprising MIT to a composition comprising a primer. In some embodiments, methods comprise adding a composition comprising MIT to a composition comprising a probe. In some embodiments, methods comprise adding a composition comprising MIT to a composition comprising an intercalating dye. In some embodiments, methods comprise adding a composition comprising MIT to a composition comprising a polymerase. In some embodiments, methods comprise adding a composition comprising 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT to a composition comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid).

In some embodiments, methods comprise storing a composition comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid) and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT for 1 to 60 minutes (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, or 60.0 minutes), 1 to 24 hours (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, or 24.0 hours), 1 to 30 days (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days), 1 to 12 months (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, or 12.0 months), or 1 to 10 years (e.g., 1.00, 1.25, 1.50, 1.75, 2.00, 2.25, 2.50, 2.75, 3.00, 3.25, 3.50, 3.75, 4.00, 4.25, 4.50, 4.75, 5.00, 5.25, 5.50, 5.75, 6.00, 6.25, 6.50, 6.75, 7.00, 7.25, 7.50, 7.75, 8.00, 8.25, 8.50, 8.75, 9.00, 9.25, 9.50, 9.75, or 10.00 years).

In some embodiments, methods comprise storing a composition comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid) and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT at −5 to 30° C. (e.g., −5.0, −4.5, −4.0, −3.5, −3.0, −2.5, −2.0, −1.5, −1.0, −0.5, 0.0, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, or 30.0° C.).

In some embodiments, methods comprise storing a composition comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid) and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT at −5 to 30° C. (e.g., −5.0, −4.5, −4.0, −3.5, −3.0, −2.5, −2.0, −1.5, −1.0, −0.5, 0.0, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, or 30.0° C.) for 1 to 60 minutes (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, or 60.0 minutes), 1 to 24 hours (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, or 24.0 hours), 1 to 30 days (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days), 1 to 12 months (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, or 12.0 months), or 1 to 10 years (e.g., 1.00, 1.25, 1.50, 1.75, 2.00, 2.25, 2.50, 2.75, 3.00, 3.25, 3.50, 3.75, 4.00, 4.25, 4.50, 4.75, 5.00, 5.25, 5.50, 5.75, 6.00, 6.25, 6.50, 6.75, 7.00, 7.25, 7.50, 7.75, 8.00, 8.25, 8.50, 8.75, 9.00, 9.25, 9.50, 9.75, or 10.00 years).

In some embodiments, methods comprise storing a composition having a volume of 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nl, gl, ml, or L and comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid) and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT for 1 to 60 minutes (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, or 60.0 minutes), 1 to 24 hours (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, or 24.0 hours), 1 to 30 days (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days), 1 to 12 months (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, or 12.0 months), or 1 to 10 years (e.g., 1.00, 1.25, 1.50, 1.75, 2.00, 2.25, 2.50, 2.75, 3.00, 3.25, 3.50, 3.75, 4.00, 4.25, 4.50, 4.75, 5.00, 5.25, 5.50, 5.75, 6.00, 6.25, 6.50, 6.75, 7.00, 7.25, 7.50, 7.75, 8.00, 8.25, 8.50, 8.75, 9.00, 9.25, 9.50, 9.75, or 10.00 years).

In some embodiments, methods comprise storing a composition having a volume of 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nl, μl, ml, or L and comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid) and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT at −5 to 30° C. (e.g., −5.0, −4.5, −4.0, −3.5, −3.0, −2.5, −2.0, −1.5, −1.0, −0.5, 0.0, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, or 30.0° C.) for 1 to 60 minutes (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, or 60.0 minutes), 1 to 24 hours (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, or 24.0 hours), 1 to 30 days (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days), 1 to 12 months (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, or 12.0 months), or 1 to 10 years (e.g., 1.00, 1.25, 1.50, 1.75, 2.00, 2.25, 2.50, 2.75, 3.00, 3.25, 3.50, 3.75, 4.00, 4.25, 4.50, 4.75, 5.00, 5.25, 5.50, 5.75, 6.00, 6.25, 6.50, 6.75, 7.00, 7.25, 7.50, 7.75, 8.00, 8.25, 8.50, 8.75, 9.00, 9.25, 9.50, 9.75, or 10.00 years).

In some embodiments, the technology provides a method comprising aliquoting a composition comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid) and 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT into a plurality of smaller volumes.

In some embodiments, methods comprise thermocycling a composition as described herein, e.g., as provided by a method described herein. In some embodiments, methods comprise recording fluorescence emission as a function of time and/or cycle number, e.g., to provide realtime PCR and/or realtime RT-PCR data.

In some embodiments, sample preparation and assay performance are automated (e.g., using automated sample handling, amplification, and analysis systems). In some embodiments, commercially available systems (e.g., available from Abbott, Abbott Park, Ill.; see, e.g., U.S. Pat. No. 8,703,445; incorporated herein by reference) are utilized.

In some embodiments, the technology comprises software and a computer processor and display screen (e.g., computer, laptop, smart phone, tablet, etc.) for analyzing and displaying data.

In some embodiments, assay components are provided in the form of a system or kit. In some embodiments, kits comprise assay reagents (e.g., nucleic acid primers or probes, buffers, controls, dNTPs, etc.), controls, software, instructions, etc. In some embodiments, reagents are provided in one or more separate containers (e.g., vials, wells, tubes, etc.). For example, in some embodiments, reagents are each provided in separate containers.

In some embodiments, the technology provides a kit comprising one or more compositions as described herein (e.g., a composition comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid)), wherein at least one of the compositions of the kit comprises 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT. In some embodiments, one or more, two or more, three or more, or four or more compositions comprise MIT. In some embodiments, one composition comprises MIT.

In some embodiments, the technology provides a system comprising one or more compositions as described herein (e.g., a composition comprising one or more components of a PCR (e.g., polymerase, primers, probes, nucleotides (e.g., one or more of dATP, dCTP, dGTP, and dTTP monomers), intercalating dye, water, buffer, sample, and/or target nucleic acid)), wherein at least one of the compositions of the kit comprises 0.0001, 0.0002, 0.0003, 0.0004, 0.0005, 0.0006, 0.0007, 0.0008, 0.0009, 0.0010, 0.0011, 0.0012, 0.0013, 0.0014, 0.0015, 0.0016, 0.0017, 0.0018, 0.0019, 0.0020, 0.0021, 0.0022, 0.0023, 0.0024, 0.0025, 0.0026, 0.0027, 0.0028, 0.0029, 0.0030, 0.0031, 0.0032, 0.0033, 0.0034, 0.0035, 0.0036, 0.0037, 0.0038, 0.0039, 0.0040, 0.0041, 0.0042, 0.0043, 0.0044, 0.0045, 0.0046, 0.0047, 0.0048, 0.0049, 0.0050, 0.0051, 0.0052, 0.0053, 0.0054, 0.0055, 0.0056, 0.0057, 0.0058, 0.0059, 0.0060, 0.0061, 0.0062, 0.0063, 0.0064, 0.0065, 0.0066, 0.0067, 0.0068, 0.0069, 0.0070, 0.0071, 0.0072, 0.0073, 0.0074, 0.0075, 0.0076, 0.0077, 0.0078, 0.0079, 0.0080, 0.0081, 0.0082, 0.0083, 0.0084, 0.0085, 0.0086, 0.0087, 0.0088, 0.0089, 0.0090, 0.0091, 0.0092, 0.0093, 0.0094, 0.0095, 0.0096, 0.0097, 0.0098, 0.0099, 0.0100, 0.0101, 0.0102, 0.0103, 0.0104, 0.0105, 0.0106, 0.0107, 0.0108, 0.0109, 0.0110, 0.0111, 0.0112, 0.0113, 0.0114, 0.0115, 0.0116, 0.0117, 0.0118, 0.0119, 0.0120, 0.0121, 0.0122, 0.0123, 0.0124, 0.0125, 0.0126, 0.0127, 0.0128, 0.0129, 0.0130, 0.0131, 0.0132, 0.0133, 0.0134, 0.0135, 0.0136, 0.0137, 0.0138, 0.0139, 0.0140, 0.0141, 0.0142, 0.0143, 0.0144, 0.0145, 0.0146, 0.0147, 0.0148, 0.0149, or 0.0150% (w/w) MIT. In some embodiments of systems, systems comprise said compositions and one or more of a thermocycler, a fluorescence detector, a computer, software for controlling said thermocycler and/or said fluorescence detector, a display, a pipettor, sample vessels, tubes configured for holding a master mix, a refrigerator, storage unit, incubator, and/or a freezer.

The technology finds use in the production of master mixes for commercial scale manufacturing of reagents for nucleic acid amplification (e.g., PCR (e.g., RT-PCR)) and in the use of nucleic acid amplification by end users (e.g., researchers, clinicians, etc.)

In some embodiments, the technology is useful for PCR. Certain basic principles of PCR that may find use in embodiments herein are described, for example, in U.S. Pat. Nos. 4,683,195; 4,683,202; 4,800,159; and 4,965,188, each of which is incorporated by reference in its entirety. Basic PCR is used to amplify a sample of target DNA for analysis or other uses. PCR uses multiple cycles of denaturation, annealing of primer pairs to opposite strands, and primer extension to increase copy numbers of a target nucleic acid sequence exponentially. The basic PCR reaction involves copying the strands of the target DNA and then using the copies to generate additional copies in subsequent cycles. The temperature of a double-stranded target DNA is elevated to a "denaturing temperature" (e.g., 85° C., 86° C., 87° C., 88° C., 89° C., 90° C., 91° C., 92° C., 93° C., 94° C., 95° C., 97° C., 98° C., 99° C., or ranges therebetween (e.g., 92-97° C.)) to denature the DNA and the temperature is then reduced to an "annealing temperature" (e.g., 48° C., 50° C., 52° C., 54° C., 56° C., 58° C., 60° C., 61° C., 62° C., 63° C., 64° C., 65° C., 66° C., 67° C., 68° C., 69° C., 70° C., 72° C., 74° C., or ranges therebetween (e.g., 62-72° C.)) to anneal at least one primer to each strand of the denatured target DNA. In some embodiments, primers are used as a pair—a forward primer and a reverse primer—and can be referred to as a primer pair or primer set. In some embodiments, the primer set comprises a 5' upstream primer that is capable of hybridizing with the 5' end of one strand of the denatured target DNA and a 3' downstream primer that is capable of hybridizing with the 3' end of the other strand of the denatured target DNA. Once a given primer binds to the strand of the denatured target DNA, the primer is extended by the action of a polymerase (e.g., at the annealing temperature or at a distinct "extension temperature" (e.g., 65° C., 66° C., 67° C., 68° C., 69° C., 70° C., 71° C., 72° C., 73° C., 74° C., 75° C., or ranges therebetween). In some embodiments, the polymerase is a thermostable DNA polymerase, for example, a Taq polymerase (or suitable variants thereof (e.g., AMPLITAQ GOLD, CRIMSON TAQ, DEEP VENTR, etc.)). The product of extension, which sometimes may be referred to as an amplicon, is then denatured from the resultant strands and the process is repeated. In some embodiments, the devices and methods provided herein are useful for the cycling of a nucleic-acid-containing sample through the various temperature steps of a PCR reaction. In some embodiments, the PCR is a reverse transcriptase polymerase chain reaction ("RT-PCR"), which is known in the art; see, e.g., Bustin (2000) "Absolute quantification of mRNA using real-time reverse transcription polymerase chain reaction assays" Journal of Molecular Endocrinology 25: 169-93, incorporated herein by reference.

Although the disclosure herein refers to certain illustrated embodiments, it is to be understood that these embodiments are presented by way of example and not by way of limitation.

EXAMPLES

Example 1

During the development of embodiments of the technology provided herein, experiments were conducted in which master mixes comprising 0, 0.015, 0.05, and 0.1% (w/w) PROCLIN 950 (corresponding to 0, 0.0015, 0.005, and 0.01% (w/w) MIT concentrations, respectively) were used to prepare RT-PCR reaction mixtures that did not comprise template (2 replicates per condition). The primers and probes in the reaction mixtures target HIV-1 nucleic acids. The fluorescent DNA-intercalating dye, EVA Green, was included in each reaction to monitor the accumulation of non-specific amplification products. Realtime EVA Green fluorescence signals from RT-PCR reactions comprising 0, 0.15, 0.05. and 0.1% (w/w) PROCLIN 950 are shown in FIG. 1. Master mixes comprising MIT (from addition of PROCLIN 950) exhibited decreased levels of non-specific product formation (as demonstrated by delayed EVA Green signals) compared to reactions that did not comprise MIT.

Example 2

Figure 2:
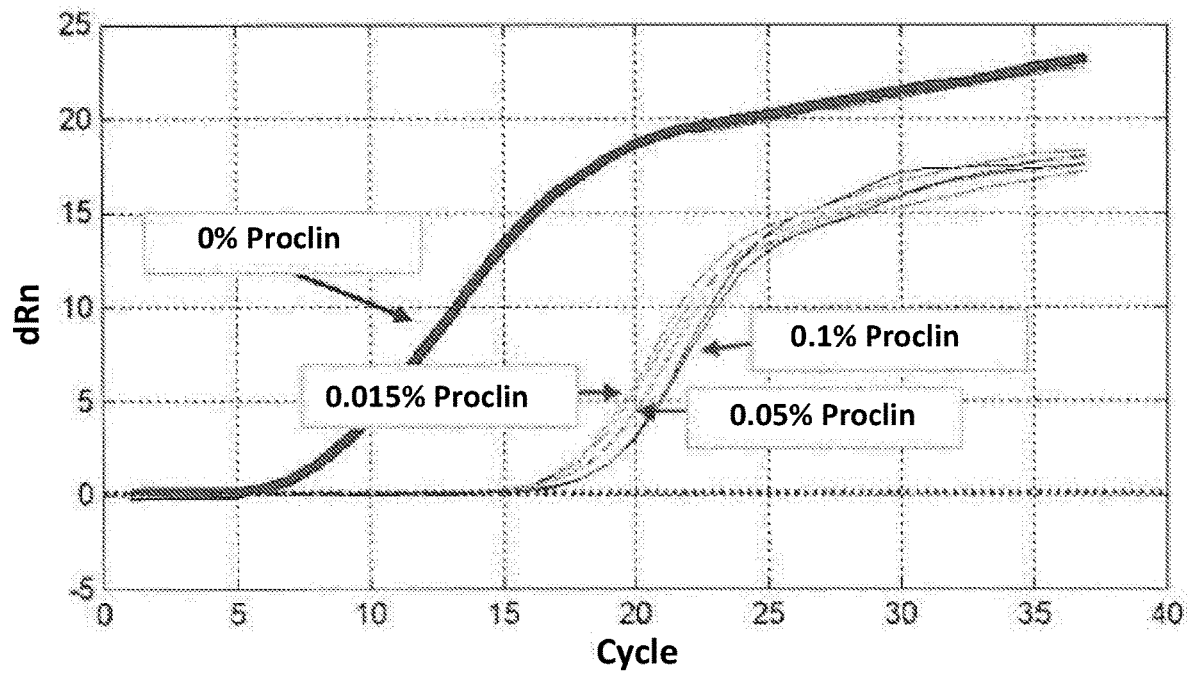
FIG. 2 is a plot of RT-PCR data showing that including MIT in RT-PCR master mixes reduces the accumulation of non-specific product during prolonged storage. The plot shows dRn as a function of cycle number for samples comprising 0, 0.015, 0.05, and 0.1% (w/w) PROCLIN 950 (corresponding to 0, 0.0015, 0.005, and 0.01% (w/w) MIT concentrations, respectively).

During the development of embodiments of the technology provided herein, experiments were conducted to simulate the preparation of bulk RT-PCR reagents by a commercial manufacturing process. In particular, prototype HIV-1 assay master mixes comprising 0, 0.015, 0.05, and 0.1% (w/w) PROCLIN 950 (corresponding to 0, 0.0015, 0.005, and 0.01% (w/w) MIT concentrations, respectively) were incubated at 2 to 8° C. for 16 hours. RT-PCR was then performed with each master mix in the absence of HIV-1 target RNA (2 replicates per condition). The fluorescent DNA-intercalating dye. EVA Green was included in each reaction to monitor the accumulation of non-specific amplification products. Realtime EVA Green fluorescence signals from RT-PCR reactions comprising 0, 0.015, 0.05, and 0.1% (w/w) PROCLIN 950 are shown in FIG. 2. Master mixes comprising MIT exhibited decreased levels of non-specific product formation (as demonstrated by delayed EVA Green signals) compared to reactions that did not comprise MIT. The data also indicated that the difference in the Ct value for reactions with MIT and without MIT was more pronounced in this experiment compared to the experiment described in Example 1. Accordingly, the data indicated that MIT and/or PROCLIN 950 provided improved stability to the master mix.

Example 3

During the development of embodiments of the technology provided herein, experiments were conducted to test RT-PCR in the presence of MIT in a prototype HIV-1 assay master mix. Prototype HIV-1 assay master mixes comprising 50 copies of HIV-1 target RNA and either 0.015% (w/w) PROCLIN 950 (0.0015% (w/w) MIT) or comprising no PROCLIN 950 were tested by RT-PCR (8 replicates each condition). HIV-specific realtime fluorescence signals from HIV-1 RT-PCR reactions comprising 0 or 0.015% (w/w)

Figure 3:
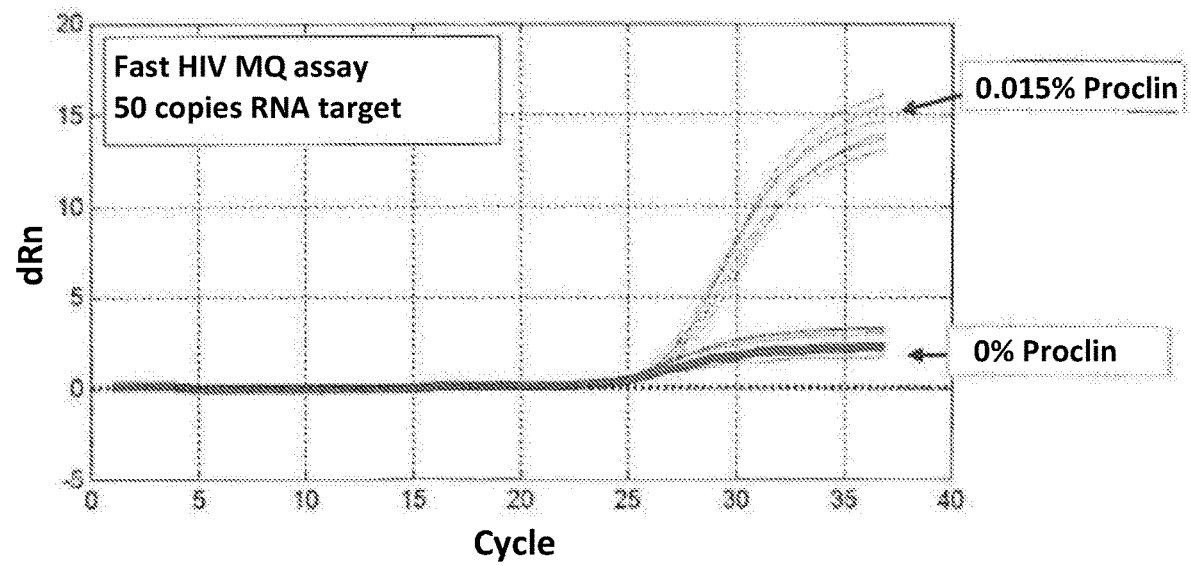
FIG. 3 is a plot of RT-PCR data indicating that adding MIT to HIV-1 assay master mixes enhances RT-PCR performance. The plot shows dRn as a function of cycle number for samples comprising 50 copies of HIV-1 target RNA and either comprising 0.015% (w/w) PROCLIN 950 (0.0015% (w/w) MIT) or comprising no PROCLIN 950.

PROCLIN 950 are shown in FIG. 3. The data indicated that RT-PCR comprising PROCLIN 950 exhibited increased signal compared to reactions containing no PROLCIN.

Example 4

Figure 4:
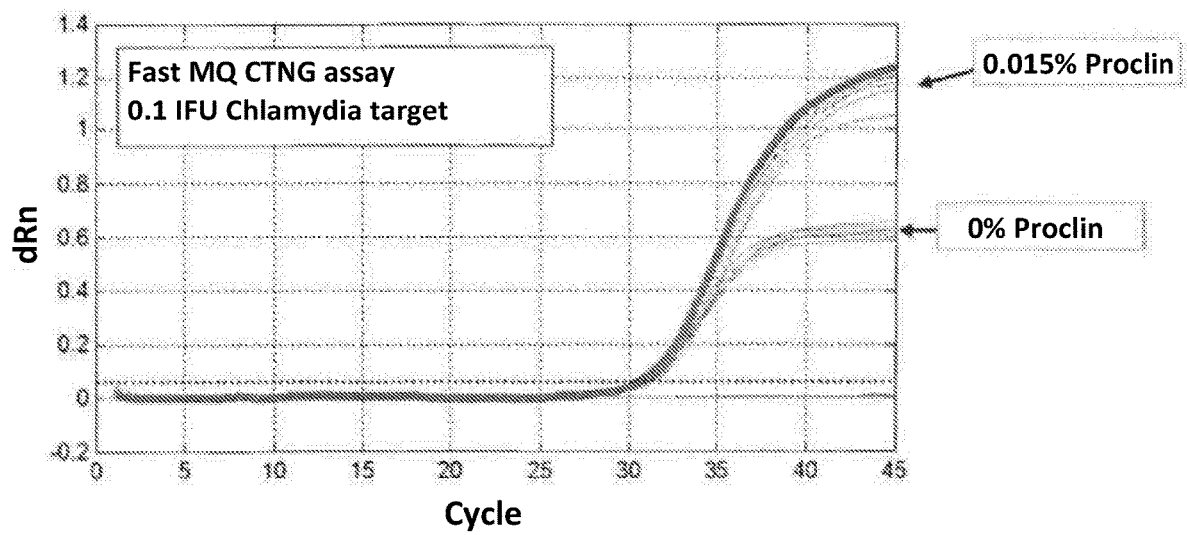
FIG. 4 is a plot of RT-PCR data indicating that adding MIT to CT/NG (*Chlamydia trachomatis* and *Neisseria gonorrhoeae*) master mixes enhances RT-PCR performance. The plot shows dRn as a function of cycle number for samples comprising 0.1 inclusion forming units of *Chlamydia trachomatis* and either comprising 0.015% (w/w) PROCLIN 950 (0.0015% (w/w) MIT) or comprising no PROCLIN 950.

During the development of embodiments of the technology provided herein, experiments were conducted to test RT-PCR in the presence of MIT in a prototype CT/NG assay master mix. Prototype CT/NG assay master mixes comprising 0.1 inclusion forming units of *Chlamydia trachomatis* and either 0.015% (w/w) PROCLIN 950 (0.0015% (w/w) MIT) or comprising no PROCLIN 950 were tested by RT-PCR (8 replicates each condition). CT-specific realtime fluorescence signals from CT/NG RT-PCR reactions comprising 0 or 0.015% (w/w) PROCLIN 950 (0.0015% (w/w) MIT) are shown in FIG. 4. The data indicated that reactions comprising PROCLIN 950 exhibited improved signal compared to reactions containing no PROCLIN 950. Further, the prototype CT/NG assay uses different primer and probe sets than the prototype HIV-1 assay described in Example 3. Accordingly, the data indicated that the PCR enhancing function of MIT is not limited to specific primer/probe sequences.

Example 5

Figure 5:
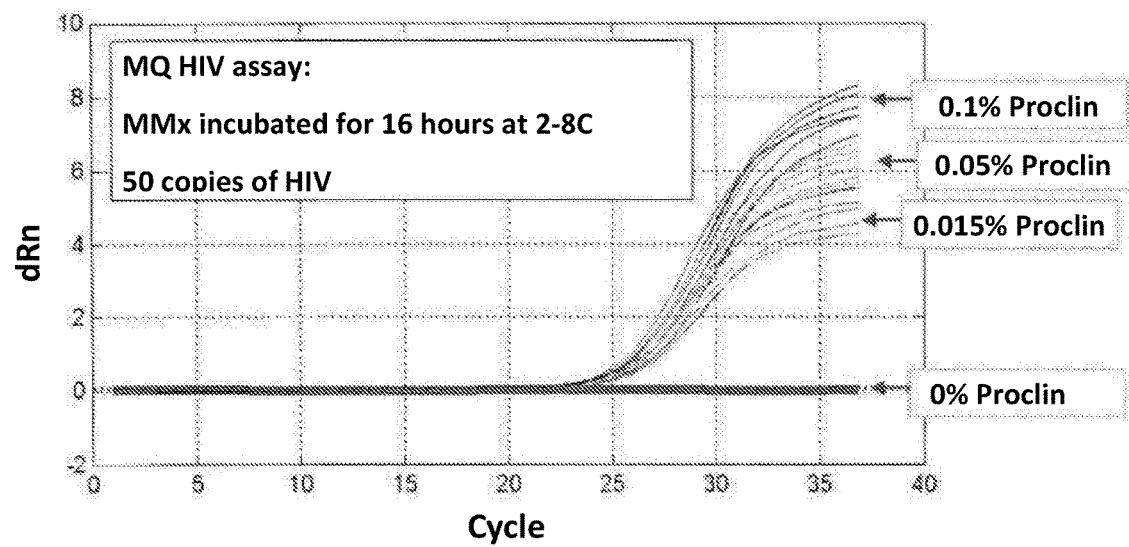
FIG. 5 is a plot of RT-PCR data indicating that MIT improves stability of PCR mastermixes. The plot shows dRn as function of cycle number for master mixes comprising 0, 0.015, 0.05, and 0.1% (w/w) PROCLIN 950 (corresponding to 0, 0.0015, 0.005, and 0.01% (w/w) MIT concentrations, respectively) that were incubated at 2 to 8° C. for 16 hours prior to use in reaction mixtures comprising 50 copies of HIV-1 RNA.

During the development of embodiments of the technology provided herein, experiments were conducted to simulate producing a bulk PCR reagent for a HI V-I assay. In particular, master mixes comprising 0, 0.015, 0.05, and 0.1% (w/w) PROCLIN 950 (corresponding to 0, 0.0015, 0.005, and 0.01% (w/w) MIT concentrations, respectively) were incubated at 2 to 8° C. for 16 hours. RT-PCR was then performed with each master mix using 50 copies of HIV-1 RNA (8 replicates per condition). HIV-specific realtime fluorescence signals from HIV-1 RT-PCR reactions comprising 0, 0.015, 0.05, and 0.1% (w/w) PROCLIN 950 are shown in FIG. 5. The data indicated that master mixes comprising PROCLIN 950 exhibited improved stability (as demonstrated by the increase signal of the RT-PCR curves) compared to reactions containing no PROCLIN 950.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A nucleic acid amplification composition comprising a polymerase, a first primer, a second primer, nucleotides, and 0.0001 to 0.01% (w/w) 2-methyl-4-isothiazolin-3-one (MIT).

2. The nucleic acid amplification composition of claim 1 further comprising a target template.

3. The nucleic acid amplification composition of claim 1 further comprising a detectably labeled probe or intercalating dye.

4. The nucleic acid amplification composition of claim 1, wherein said composition does not comprise a primer dimer comprising said first primer and said second primer.

5. An oligonucleotide reagent comprising a first primer, a second primer, a detectably labeled probe, nucleotides, and 0.0001 to 0.01% (w/w) MIT.

6. The oligonucleotide reagent of claim 5 further comprising a second detectably labeled probe.

7. The oligonucleotide reagent of claim 5 further comprising a reference dye.

8. The oligonucleotide reagent of claim 5 further comprising a third primer and a fourth primer.

9. A kit comprising:
   a) an oligonucleotide reagent comprising a first primer, a second primer, a detectably labeled probe, nucleotides, and 0.0001 to 0.01% (w/w) MIT; and
   b) an activation reagent comprising manganese chloride and 0.0001 to 0.1% (w/w) MIT.

10. The kit of claim 9 further comprising a thermostable polymerase in a buffered solution.

11. The kit of claim 10 wherein said thermostable polymerase is rTth polymerase.

12. The kit of claim 9 further comprising an internal control comprising a control nucleic acid and 0.0001 to 0.01% (w/w) MIT.

* * * * *